(12) United States Patent
Kim et al.

(10) Patent No.: US 12,410,419 B2
(45) Date of Patent: Sep. 9, 2025

(54) USE OF ENZYME THAT CLEAVES BOTH ALPHA- AND BETA- 1,4-GLYCOSIDIC BONDS

(71) Applicant: Korea University Research and Business Foundation, Seoul (KR)

(72) Inventors: Kyoung Heon Kim, Seoul (KR); Do Hyoung Kim, Yongin-si (KR)

(73) Assignee: Korea University Research and Business Foundation, Seoul (KR)

( * ) Notice: Subject to any disclaimer, the term of this patent is extended or adjusted under 35 U.S.C. 154(b) by 962 days.

(21) Appl. No.: 17/595,616

(22) PCT Filed: May 21, 2020

(86) PCT No.: PCT/KR2020/006649
§ 371 (c)(1),
(2) Date: Apr. 8, 2022

(87) PCT Pub. No.: WO2020/235946
PCT Pub. Date: Nov. 26, 2020

(65) Prior Publication Data
US 2022/0243188 A1  Aug. 4, 2022

(30) Foreign Application Priority Data
May 21, 2019 (KR) .......................... 10-2019-0059565

(51) Int. Cl.
*C12N 9/24* (2006.01)
*C12N 15/63* (2006.01)
(52) U.S. Cl.
CPC ............... *C12N 9/24* (2013.01); *C12N 15/63* (2013.01); *C12Y 302/01051* (2013.01)
(58) Field of Classification Search
None
See application file for complete search history.

(56) References Cited

U.S. PATENT DOCUMENTS 8,771,996 B2 * 7/2014 Kim .......................... C12N 1/20
435/105

FOREIGN PATENT DOCUMENTS

JP 7-236480 A 9/1995
KR 10-2016-0065111 A 6/2016

OTHER PUBLICATIONS

Office Action issued Feb. 21, 2023 in Japanese Application No. 2021-569130.
"*Vibrio* sp. EJY3 chromosome 1, complete sequence", National Center for Biotechnology Information, GenBank: CP003241.1, Jan. 30, 2014 (7 pages total).
Hanseong Roh et al., "Genome Sequence of *Vibrio* sp. Strain EJY3, an Agarolytic Marine Bacterium Metabolizing 3,6-Anhydro-L-Galactose as a Sole Carbon Source", Journal of Bacteriology, 2012, pp. 2773-2774 (2 pages total).
Mateusz Lezyk et al., "Novel a-L-Fucosidases from a Soil Metagenome for Production of Fucosylated Fluman Milk Oligosaccharides", PLOS One, Jan. 22, 2016, pp. 1-18.
Eva Benesova et al., "a-L-Fucosidase from Paenibacillus thiaminolyticus: Its hydrolytic and transglycosylation abilities", Glycobiology, May 30, 2013, pp. 1052-1065, vol. 23, No. 9.
Za Megson et al., "Characterization of an a-i-fucosidase from the periodontal pathogen Tannerella forsythia", Virulence, Apr. 2015, pp. 282-292, vol. 6, No. 3.
"TPA: alpha-L-fucosidase [Porphyromonadaceae bacterium]", NCBI, GenBank: HBB01954.1, Sep. 6, 2018, 2 pgs.
International Search Report for PCT/KR2020/006649 dated, Sep. 1, 2020 (PCT/ISA/210).

* cited by examiner

*Primary Examiner* — Vera Afremova
(74) *Attorney, Agent, or Firm* — Sughrue Mion, PLLC

(57) ABSTRACT

The present invention relates to use of an enzyme that cleaves both alpha- and beta-1,4-glycosidic bonds and, more particularly, the present invention provides α-L-fucosidase which has α-1,4-glucosidase and β-1,4-galactosidase activities and thus is capable of producing glucose and/or galactose, which are monosaccharides, from non-fucosylated saccharides. The enzyme has transglycosylation activity and thus produces maltooligosaccharides having a higher degree of polymerization than maltooligosaccharides used as a substrate, thereby being applicable to the development of high-value-added new materials in the food industry.

10 Claims, 8 Drawing Sheets
Specification includes a Sequence Listing.

USE OF ENZYME THAT CLEAVES BOTH ALPHA- AND BETA- 1,4-GLYCOSIDIC BONDS

CROSS REFERENCE TO RELATED APPLICATIONS

This application is a National Stage of International Application No. PCT/KR2020/006649, filed May 21, 2020, claiming priority to Korean Patent Application No. 10-2019-0059565, filed May 21, 2019, the entire disclosures of which are incorporated herein by reference.

BACKGROUND

1. Field of the Invention

The present invention relates to use of an enzyme that cleaves both alpha- and beta-1,4-glycosidic bonds.

2. Discussion of Related Art

α-L-Fucosidase (3.2.1.51) is an exo-glycosyl hydrolase capable of catalyzing the hydrolysis of α-linked-L-fucosyl residues from the non-reducing ends of different types of fucosylated oligosaccharides and fucoglyco conjugates. According to the type of reaction catalyzed by an enzyme and its specificity for a substrate, fucosidases are classified into α-1,2-L-fucosidase (EC 3.2.1.63) that cleaves α-1,2 bonds between fucose and galactose, α-1,3-fucosidase (3.2.1.111) that cleaves α-1,3 bonds between fucose and N-acetylglucosamine (GlcNAc), and α-L-fucosidase (EC 3.2.1.51) with low specificity, capable of cleaving various categories of bonds such as α-1,2 bonds between fucose and galactose and α-1,3/4/6 bonds between fucose and GlcNAc. According to the classification of the Carbohydrate-Active EnZymes(CAZy)) database (http://vww.cazy.org/Glycoside-Hydrolases.html), α-L-fucosidase belongs to the GH families 29 (GH29) and 95 (GH95), which have different mechanisms used for different hydrolysis reaction catalysts. The α-L-fucoside of GH95 hydrolyzes α-1,2 fucosyl bonds found in the sugar chains of various oligosaccharides and glycoproteins, particularly through a direct substitution (inversion) mechanism. Conversely, a hydrolysis reaction mediated by the α-L-fucosidase of GH29 occurs through the classical Koshland double-substitution mechanism where the configuration of a substrate anomeric center is retained in the resulting product. Interestingly, a retaining enzyme of GH29 can catalyze not only a hydrolysis reaction, but also transglycosylation, that is, a reaction in which a final acceptor of a cleaved glycoside residue is a hydroxyl group-containing molecule different from water. Recently, GH29 has been classified into two subfamilies, GH subfamilies 29A and 29B, based on substrate specificity and sequence homology. The GH subfamily 29A includes α-L-fucosidase, may act on a synthetic substrate such as p-nitrophenyl-α-L-fucopyranoside (pNP-α-L-Fuc), and has a limited ability to hydrolyze fucosyl oligosaccharides. The GH family 29B includes α-L-fucosidase, is more position-specific for α-1, 3/4 fucosyl bonds with a branched galactose residue at the non-reducing end, and cannot substantially hydrolyze pNP-α-L-Fuc.

α-L-fucosidase has been isolated from a wide range of organisms, including bacteria, fungi, plants, marine invertebrates and mammals. Recently, α-L-fucosidase has been cloned and characterized from several intestinal bacteria, including *Bifidobacterium*, *Bacteroides* and *Lactobacillus*.

Further, the relationship between α-L-fucosidase and fucosyl glycan degradation by some intestinal microorganisms has been reported. To date, all reported α-L-fucosidases catalyze the removal of terminal fucosyl bonds of oligosaccharides or their conjugates, but their ability to hydrolyze non-fucosylated substrates has not been reported.

SUMMARY OF THE INVENTION

An object of the present invention is to provide use of a novel fucosidase derived from *Vibrio* sp. having dual glycosidic hydrolytic activity.

In order to achieve the object, the present invention provides a composition for producing monosaccharides or maltooligosaccharides, including: α-L-fucosidase including an amino acid sequence of SEQ ID NO: 1; and one or more substrates selected from the group consisting of lactose and maltooligosaccharides having a degree of polymerization of 2 or higher.

The present invention also provides a use of α-L-fucosidase including an amino acid sequence of SEQ ID NO: 1 for producing monosaccharides or maltooligosaccharides.

The present invention also provides a method for producing monosaccharides or maltooligosaccharides, the method including: reacting one or more substrates selected from the group consisting of lactose and maltooligosaccharides having a degree of polymerization of 2 or higher with α-L-fucosidase including an amino acid sequence of SEQ ID NO: 1; and collecting monosaccharides and maltooligosaccharides from a reaction product, wherein the maltooligosaccharides have a higher degree of polymerization than that of maltooligosaccharides used as the substrate.

The α-L-fucosidase of the present invention has α-1,4-glucosidase and β-1,4-galactosidase activities and thus produces glucose and galactose, which are monosaccharides, from non-fucosylated saccharides. The enzyme has transglycosylation activity and thus produces maltooligosaccharides having a higher degree of polymerization than maltooligosaccharides used as a substrate, thereby being applicable to the development of high-value-added new materials in the food industry.

BRIEF DESCRIPTION OF THE DRAWINGS

FIGS. 4A-4I illustrate the results of measuring the relative activity of VeFUC reacted with (FIG. 4A) pNP-α-L-fuc, (FIG. 4B) lactose and (FIG. 4C) maltose at different pHs; the relative activity of VeFUC reacted with (FIG. 4D) pNP-α-L-fuc, (FIG. 4E) lactose and (FIG. 4F) maltose at different temperatures; and the relative activity of VeFUC pre-incubated at different temperatures for 60 minutes in order to determine the thermal stability of VeFUC using (FIG. 4G) pNP-α-L-fuc, (FIG. 4H) lactose and (FIG. 4I) maltose. Data represents the mean±standard deviation of three replicates.

DETAILED DESCRIPTION OF EXEMPLARY EMBODIMENTS

Figure 1:
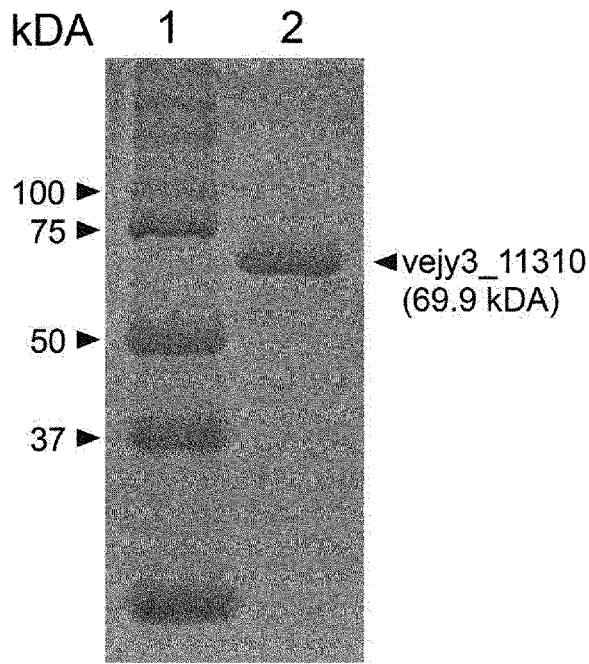
FIG. 1 illustrates the expression of VeFUC using SDS-PAGE. Lane 1 is a protein marker, and Lane 2 is VeFUC purified by His-tag affinity chromatography.

Hereinafter, the configuration of the present invention will be described in detail.

The present invention relates to a composition for producing monosaccharides or maltooligosaccharides, including: α-L-fucosidase including an amino acid sequence of SEQ ID NO: 1; and one or more substrates selected from the group consisting of lactose and maltooligosaccharides having a degree of polymerization of 2 or higher.

Further, the present invention provides a use of α-L-fucosidase including an amino acid sequence of SEQ ID NO: 1 for producing monosaccharides or maltooligosaccharides.

The present invention also provides a method for producing monosaccharides or maltooligosaccharides, the method including: reacting one or more substrates selected from the group consisting of lactose and maltooligosaccharides having a degree of polymerization of 2 or higher with α-L-fucosidase including an amino acid sequence of SEQ ID NO: 1; and collecting monosaccharides and maltooligosaccharides from a reaction product, wherein the maltooligosaccharides have a higher degree of polymerization than that of maltooligosaccharides used as the substrate.

As a result of being characterized by cloning and expressing α-L-fucosidase, VeFUC derived from the marine bacterium *Vibrio* sp. strain EJY3, the present inventors reported for the first time that α-L-fucosidase can hydrolyze a non-fucosylated substrate to monosaccharides glucose and/or galactose by α-1,4 glucosidase and β-1,4 galactosidase activities. In addition, the enzyme has transglycosylation activity and thus can produce oligosaccharides having a higher degree of polymerization than a substrate.

According to an exemplary embodiment of the present invention, as a result of measuring the hydrolytic activity for a synthetic substrate or natural disaccharides, the α-L-fucosidase showed high relative activity for pNP-α-L-Fuc, pNP-α-D-Glc, and pNP-β-D-Gal, but did not show any activity for pNP-α-D-Gal and pNP-β-D-Glc, among synthetic substrates, for example, pNP-α-L-Fuc, pNP-α-D-Glc, pNP-β-D-Glc, pNP-α-D-Gal, and pNP-β-D-Gal. Furthermore, when disaccharides having various types of glycosidic bonds were used as a substrate, lactose (β-1,4-glycosidic bond) and maltose (α-1,4-glycosidic bond) were hydrolyzed by VeFUC, but sucrose having α-1,2-glycosidic bonds, laminaribiose having β-1,3-glycosidic bonds, and cellobiose having β-1,4-glycosidic bonds, which consist of two units of D-glucose, were not hydrolyzed. Therefore, it can be seen that the α-L-fucosidase has α-fucosidase, α-1,4-glucosidase and β-1,4-galactosidase activities, but does not have α-galactosidase and β-glucosidase activities.

From the results, it can be seen that the α-L-fucosidase of the present invention may use lactose having β-1,4-glycosidic bonds and maltose having α-1,4-glycosidic bonds as a bonding mode of a non-reducing end as a substrate.

Further, the optimum pH of the α-L-fucosidase in a buffer solution such as sodium acetate, Tris-HCl, and glycine-NaOH may vary depending on the type of buffer solution, but the α-L-fucosidase shows an enzyme activity of 60% or more at a pH of about 4 to 8, and specifically, shows the highest activity at a pH of about 6 to 8. According to an exemplary embodiment of the present invention, the highest activity of VeFUC for pNP-α-L-Fuc, maltose and lactose was obtained at pH 6.0 in 10 mM sodium acetate buffer solution, pH 7.0 in 10 mM Tris-HCl buffer solution, and pH 6.0 in 10 mM sodium acetate buffer solution, respectively.

The optimum temperature for the enzyme activity of the α-L-fucosidase is 30 to 40° C. and more specifically, about 30° C. As a result of a thermal stability test, α-L-fucosidase was stable at a temperature of about 30° C. or less, but relative activity decreased at a temperature higher than about 30° C. Therefore, the α-L-fucosidase is capable of sufficient enzymatic reaction even at room temperature, so there is an advantage in that a process can be economically performed without consuming energy to increase the temperature. Further, the enzyme may be inactivated by heat treatment at a relatively low temperature compared to existing enzymes.

The α-L-fucosidase may be derived from *Vibrio* sp. strain EJY3, but is not particularly limited thereto.

In addition, α-L-fucosidase may be transcribed and translated through not only a region before and after a coding region, but also a DNA segment associated with the production of a peptide including an intervening sequence between individual coding segments, that is, a coding gene. For example, the α-L-fucosidase may be transcribed and translated from the sequence set forth in SEQ ID NO: 2, but is not particularly limited thereto. Furthermore, a protein having hydrolytic activity against the monosaccharides or the maltooligosaccharides as a variant protein with one or more of substitution, deletion, transposition, addition, and the like of the enzyme is also included in the scope of rights of the enzyme of the present invention, and preferably, includes an amino acid sequence having a sequence identity of 80% or more, 85% or more, 90% or more, 93% or more, 94% or more, 95% or more, 96% or more, 97% or more, 98% or more, and 99% or more with the amino acid sequence disclosed in SEQ ID NO: 1.

The α-L-fucosidase may be isolated and purified from a supernatant of a cultured of *Vibrio* sp. strain EJY3, and may be produced and isolated by a strain other than *Vibrio* sp. strain EJY3 or an artificial chemical synthesis method, and the like using genetic engineering recombinant technology.

When recombinant technology is used, as factors used in order to facilitate the expression of a typical recombinant protein, for example, it is possible to use an antibiotic resistance gene, and a reporter protein or a peptide which may be used for affinity column chromatography, and these techniques fall within the scope that can be easily carried out by those skilled in the art to which the present invention pertains. For example, the α-L-fucosidase may be obtained from a host cell transformed with a recombinant vector including a gene encoding the α-L-fucosidase, that is, a base sequence set forth in SEQ ID NO: 2 or a culture thereof. *Escherichia coli* is used as the host cell, but the host cell is not limited thereto.

As described above, for the α-L-fucosidase of the present invention, monosaccharides may be obtained as degradation products through a hydrolysis reaction using lactose and maltose as a substrate. The monosaccharides may be glucose and/or galactose. According to an exemplary embodiment of the present invention, when lactose is used as a substrate, glucose and galactose are produced as degradation products. When maltose is used as a substrate, glucose and maltooligosaccharides having a higher degree of polymerization than a substrate are produced by α-glucosidase and transglycosylation activity.

According to an exemplary embodiment of the present invention, as a result of performing a reaction using maltose (DP2), maltotriose (DP3), and maltotetraose (DP4) in order to investigate the transglycosylation activity of the α-L-fucosidase, maltooligosaccharides having a high degree of polymerization are produced for each substrate, maltose is hydrolyzed to glucose, and maltooligosaccharides of DP3, DP4, and DP5 are produced. When maltotriose and maltotetraose are used as substrates, maltooligosaccharides of DP8 and DP9 are produced, respectively.

Therefore, the α-L-fucosidase may use lactose and maltooligosaccharides having a degree of polymerization of 2 or higher as a substrate. Preferably, the maltooligosaccharides may be maltooligosaccharides having a degree of polymerization of 2 to 4. Further, when maltooligosaccharides having a degree of polymerization of 2 to 4 are used as a substrate, as degradation products, maltooligosaccharides having a higher degree of polymerization than the substrate may be produced.

For a reaction of the α-L-fucosidase with the substrate, the maltooligosaccharides may be produced by the reaction under conditions of 30 to 40° C., a pH of 6 to 8, and 30 minutes to 48 hours. More specifically, the maltooligosacchandes may be produced by the reaction under conditions of 30 to 35° C., a pH of 6 to 8, and 30 minutes to 2 hours.

Monosaccharides or maltooligosaccharides at a high purity of approximately 95% may be separated and purified by sequentially carrying out silica gel chromatography which is absorption chromatography and Bio Gel P2 chromatography which is a gel permeation chromatography on a degradation product of the α-L-fucosidase.

As used herein, "protein" and "polypeptide" are used interchangeably in the present application.

In the present invention, the fact that a polypeptide has a sequence identity of a specific percentage (for example, 80%, 85%, 90%, 95%, or 99%) with another sequence means that when the two sequences are aligned, there is a specific percentage of identical amino acid residues at the time of comparing the sequences. The alignment and percentage homology or identity may be determined using any suitable software program publicly known in the art such as those described in, for example, a document [CURRENT PROTOCOLS IN MOLECULAR BIOLOGY (F. M. Ausubel et al., (eds) 1987 Supplement 30 section 7.7.18)]. Examples of a preferred program include a GCG Pileup program, FASTA (Pearson et al., 1988 *Pr° C. Natl Acad. Sci USA* 85:2444-2448), and BLAST (BLAST Manual, Altschul et al., Natl. Cent. Biotechnol. Inf., Natl Lib. Med. (NCIB NLM NIH), Bethesda, MD, and Altschul et al., 1997 NAR25:3389-3402). Another preferred alignment program is ALIGN Plus (Scientific and Educational Software, PA), and preferably, is an alignment program which uses default parameters. Another available sequence software program is the TFASTA Data Searching Program available in the Sequence Software Package Version 6.0 (Genetics Computer Group, University of Wisconsin, Madison, WI).

In the present invention, the term "recombinant" when used in connection with a cell, a nucleic acid, a protein, or a vector indicates that the cell, the nucleic acid, the protein, or the vector is modified by introducing a heterologous nucleic acid or protein or changing an original nucleic acid or protein, or that the cell is derived from the thus modified cell. That is, for example, a recombinant cell expresses a gene which is not found within the original (non-recombinant) form of the cell, or otherwise, the recombinant cell expresses an original gene which is abnormally expressed or not expressed at all when expressed.

As used herein. "nucleic acid" encompasses single stranded or double stranded DNA and RNA, and a chemical variant thereof. "Nucleic acid" and "polynucleotide" may be used interchangeably in the present application. Since the genetic code is degenerate, one or more codons may be used in order to encode a specific amino acid, and the present invention encompasses polynucleotides encoding a specific amino acid sequence.

The term "introduction" in which a nucleic acid sequence is inserted into a cell means "transfection", or "transformation" or "transduction", and the mention of integration of a nucleic acid sequence into an eukaryotic cell or a prokaryotic cell is included, and in this case, the nucleic acid sequence is integrated into a genome (for example, a chromosome, a plasmid, a choromatophore, or mitochondrial DNA) of a cell, and thus is converted into an autonomous replicon, or transiently expressed.

Hereinafter, the present invention will be described in more detail through the Examples according to the present invention, but the scope of the present invention is not limited by the Examples suggested below.

<Example 1> Cloning, Expression and Characterization of VeFUC (Cloning and Expression of VeFUC)

Genomic DNA of *Vibrio* sp. strain EJY3 for cloning a gene encoding VeFUC was prepared as follows: *Vibrio* sp. strain EJY3 was cultured in a minimum medium consisting of 23 g/L Instant Ocean Sea Salt (Aquarium Systems, Mentor, OH, USA), 50 mM Tris-HCl (pH 7.4), 2 g/L glucose, 1 g/L yeast extract and 0.5 g/L ammonium chloride at 303 K and 200 rpm for 18 hours. The genomic DNA was extracted from a culture using the DNeasy Blood & Tissue Kit (Qiagen, Valencia, CA, USA) according to the manufacturer's protocol. A target gene, VEJY3_11310 (UniProt accession no. H2IHW9.1) was amplified by PCR using the following primers. The underlined parts are BamHI and XhoI restriction enzyme sites;

(forward: SEQ ID NO: 3)
5'-GCG GGATCCATGACCAAGCCCACAGCAGGTG-3';

(reverse: SEQ ID NO: 4)
5'-GCG CTCGAGGTGGTGGTGGTGGTGGTGCGCCAAGCGGGGGCCCAA CTG-3'

Recombinant proteins were purified using a HisTrap column (GE Healthcare, Piscataway, NJ, USA) by adding sequences encoding 6 histidines to the reverse primer. A PCR product was treated with BamHI and XhoI restriction enzymes and subsequently ligated to a pET-21a plasmid (Novagen, Darmstadt, Germany) to construct a PET21a-VeFUC plasmid.

(Expression and Purification of VeFUC)

Recombinant *E. coli* loaded with the pET21a-VeFUC plasmid was grown at 310 K and 200 rpm until an absorbance measured at 600 nm in a culture Luria-Bertani (LB) broth containing 100 mg L$^{-1}$ ampicillin reached 0.6. The overexpression of the enzyme was induced at 289 K for 16 hours by 1 mM isopropyl-β-d-thiogalactopyranoside (IPTG) (Sigma, St. Louis, MO). Cells were collected by centrifugation at 4,000×g for 15, disrupted by ultrasound, and then centrifuged at 16,000×g for 1 hour. A cell-free coenzyme (crude enzyme) was purified using Ni-nitrilotriacetic acid (NTA) affinity chromatography (Qiagen, Valencia. CA, USA). Elution was performed using 1 mL of an elution buffer with 300 mm imidazole. The purified recombinant proteins were concentrated using an Amicon ultracentrifugal filter unit (molecular weight cutoff value of 50,000, Millipore, Billerica, MA, USA). The concentrated enzyme solution was analyzed by bicinchoninic acid (BCA) protein analysis (Thermo Fisher Scientific, Waltham, MA) and 12% (w/v) SDS-PAGE gel electrophoresis to determine the concentration, size and purity of the target protein.

(Measurement of Enzyme Activity of VeFUC)

In order to measure the enzyme activity of VeFUC, 4 nmol of VeFUC was incubated at 303 K for 60 minutes with 100 μl of 10 mM synthetic substrate, for example, p-nitrophenyl-α-L-fucopyranoside (pNP-α-L-Fuc, a substrate for analyzing α-fucosidase), p-nitrophenyl-α-D-glucopyranoside (pNP-α-D-Glc, a substrate for analyzing α-glucosidase), p-nitrophenyl-β-D-glucopyranoside (pNP-β-D-Glc, a substrate for analyzing β-glucosidase), p-nitrophenyl-α-D-galactopyranoside (pNP-α-D-Gal, a substrate for analyzing α-galactosidase) and p-nitrophenyl-β-D-galactopyranoside (pNP-β-D-Gal, a substrate for analyzing β-galactosidase) (all purchased from Sigma-Aldrich). The reaction was terminated by adding 500 μl of 1 M sodium carbonate thereto, and the absorbance of the reaction mixture was quantified by spectrophotometry at 405 nm. One unit (U) of VeFUC was defined as the amount of enzyme required to produce 1 μmol of p-nitrophenyl (pNP) per minute under the above-described enzymatic reaction conditions.

Further, in order to test the enzyme activity of VeFUC, biomass-derived disaccharides, including sucrose (formed by D-glucose and D-fructose units having α-1,2 glycosidic bonds) and maltose (formed by two D-glucoses having α-1,4 glycosidic bonds)(all purchased from Sigma), laminaribiose (formed by two D-glucoses with β-1,3 glycosidic bonds)(Megazyme, Wicklow, Ireland), lactose (formed by D-galactose and D-glucose units having β-1,4 glycosidic bonds) and cellobiose (formed by two units of D-glucose having β-1,4 glycosidic bonds), were tested. For enzymatic reaction, 4 nmol VeFUC was incubated with 100 μl of 10 mM Tris-HCl buffer (pH 7.0) containing 30 mmM of each substrate at 300 K for 60 minutes.

In order to measure the kinetic parameters of VeFUC for pNP-α-L-Fuc, enzymatic reactions were performed at different concentrations of pNP-α-L-Fuc in a range of 0.109 to 0.875 mM under the same conditions described above. $V_{max}$, $K_m$ and $k_{cat}$, which are enzyme kinetic parameters of VeFUC were measured from a Lineweaver-Burk plot.

(Analysis of Enzymatic Reaction Products by TLC and HPLC)

In order to analyze enzymatic reaction products of VeFUC, TLC and HPLC were used. For TLC analysis, 1 μl of the reaction mixture was loaded into a silica gel 60 plate (Merck, Darmstadt, Germany), and in this case, a mobile phase consisting of n-butanol/acetic acid/water (volume ratio of 3:2:2) was used, and visualized by heating a TLC plate at 403 K for 5 minutes using a 10% (v/v) sulfuric acid solution in ethanol.

Reaction products were also analyzed on an Agilent 1100 HPLC system (Agilent) equipped with a Bio-Rad Aminex HPX-87H column and a refractive index detector (Agilent Technologies, Wilmington, DE, USA). HPLC analysis was performed at 338 K and a flow rate of 0.5 mL/min using 5 mM sulfuric acid as a mobile phase.

(Analysis of Enzymatic Reaction Products by Matrix-Assisted Laser Desorption Ionization-Tandem Time of Flight Mass Spectrometry (MALDI-TOF MS))

In order to measure the transglycosylation activity of VeFUC, 4 nmol VeFUC was incubated with 30 mM maltose, maltotriose (formed by three D-glucose units having α-1,4 glycosidic bonds), or maltotetraose (formed by four D-glucose units having α-1,4 glycosidic bonds). The reaction mixture was analyzed by MALDI-TOF/TOF MS using an ultrafleXtreme MALDI-TOF/TOF MS system (Bruker Daltonics). In order to prepare a sample, reaction products were dissolved in water, 1 μl of the solubilized reaction product was added dropwise to a stainless steel target plate, and then 0.3 μl of 10 mM NaCl and 0.5 μl of 50 g/L 2,5-dihydroxybenzoic acid in 50% (v/v) acetonitrile were added thereto. Spots were quickly dried under vacuum to allow them to uniformly crystallize. Samples were analyzed by MALDI-TOF/TOF MS as previously described. Raw MS data was processed using FlexAnalysis software (version 3.3; Bruker Daltonics). All MS peaks were deconvoluted and a list of all neutral masses in the sample was generated, with abundances represented by mass spectral peak intensities.

(Characterization of VeFUC Enzyme)

In order to measure the optimum pH for VeFUC activity, 4 nmol VeFUC was incubated with each of 10 mM pNP-α-L-Fuc, 10 mM lactose and 10 mM maltose at 303 K for 10 minutes in a buffer solution with various pHs (10 mM sodium acetate (pH 4.0 to 6.0), 10 mM Tris-HCl (pH 6.0 to 9.0) and 10 mM glycine-NaOH (pH 9.0 to 10.0)).

In order to measure the optimum temperature for enzyme activity of VeFUC, 4 nmol VeFUC was incubated in a temperature range of 293 K to 343 K for 30 minutes in each of 10 mM pNP-α-L-Fuc and 10 mM lactose in 10 mM sodium acetate (pH 6.0), and 10 mM maltose in 10 mM Tris-HCl buffer (pH 7.0).

In order to measure the thermal stability of VeFUC, 4 nmol VeFUC was incubated in advance in various temperature ranges of 293 K to 343 K for 1 hour before an enzymatic reaction with each of 10 mM pNP-α-L-Fuc and 10 mM lactose in 10 mM sodium acetate (pH 6.0) and 10 mM maltose in 10 mM Tris-HCl buffer solutions (pH 7.0). The enzymatic reaction was terminated by incubating the reaction mixture in boiling water for 1 minute. The reaction mixture was analyzed by HPLC.

<Experimental Example 1> Enzyme Activity and Substrate Specificity of VeFUC The enzyme activity of VeFUC, α-L-fucosidase derived from *Vibrio* sp. strain EJY3 was characterized. For this purpose, VeFUC was expressed in the *E. coli* BL21 (DE) strain, and the molecular weight of VeFUC corresponded to its theoretical mass value, 69.9 kDa (FIG. 1). As a result of performing an enzyme analysis on each substrate including a synthetic substrate and natural disaccharides, VeFUC was confirmed to be a novel α-L-fucosidase showing unique and previously unreported activity.

Figure 2:
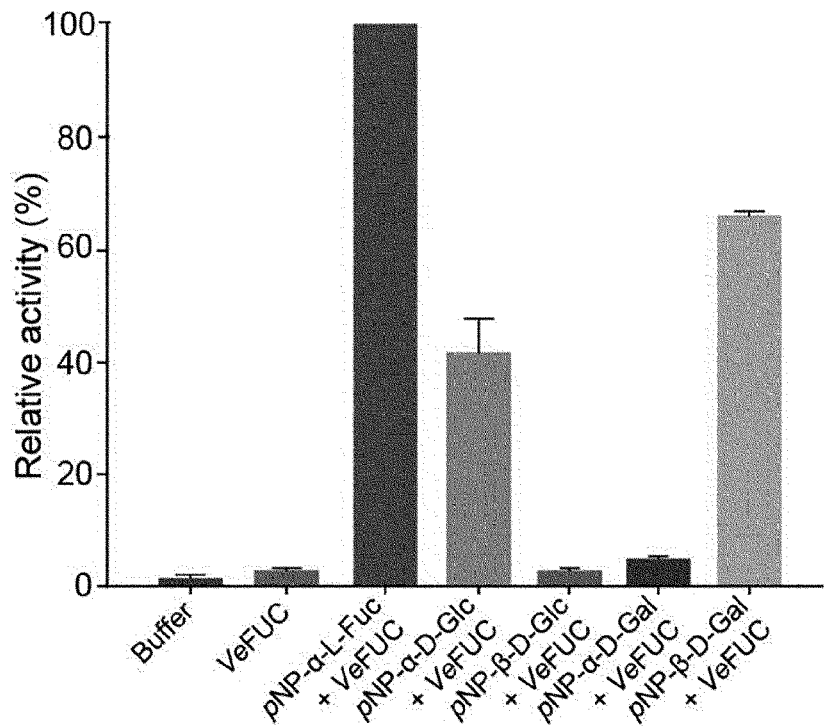
FIG. 2 illustrates the enzyme activity of VeFUC. Reactions were performed at 303 K for 60 minutes using pNP-α-L-fuc, pNP-α-D-Glc, pNP-β-D-Glc, pNP-α-D-Gal, and pNP-β-D-Gal as a substrate. Data represents the mean±standard deviation of three replicates.

In order to measure the enzyme activity of VeFUC, synthetic substrates, for example, pNP-α-L-Fuc, pNP-α-D-Glc, pNP-β-D-Glc, pNP-α-D-Gal and pNP-β-D-Gal were used for the enzymatic reaction. This class of compounds is usually used for the analysis of glycosidase activity and specificity, a p-nitrophenyl (pNP) group acts as an excellent leaving group, and may be easily quantified by spectroscopy. VeFUC showed the highest activity for pNP-α-L-Fuc, and further exhibited a relative pNP-α-D-Glc hydrolysis activity of 41.5%, and exhibited a relative activity of 65.3% for pNP-β-D-Gal (FIG. 2). However, VeFUC did not exhibit any activity for pNP-α-D-Gal and pNP-β-D-Glc.

Figure 3:
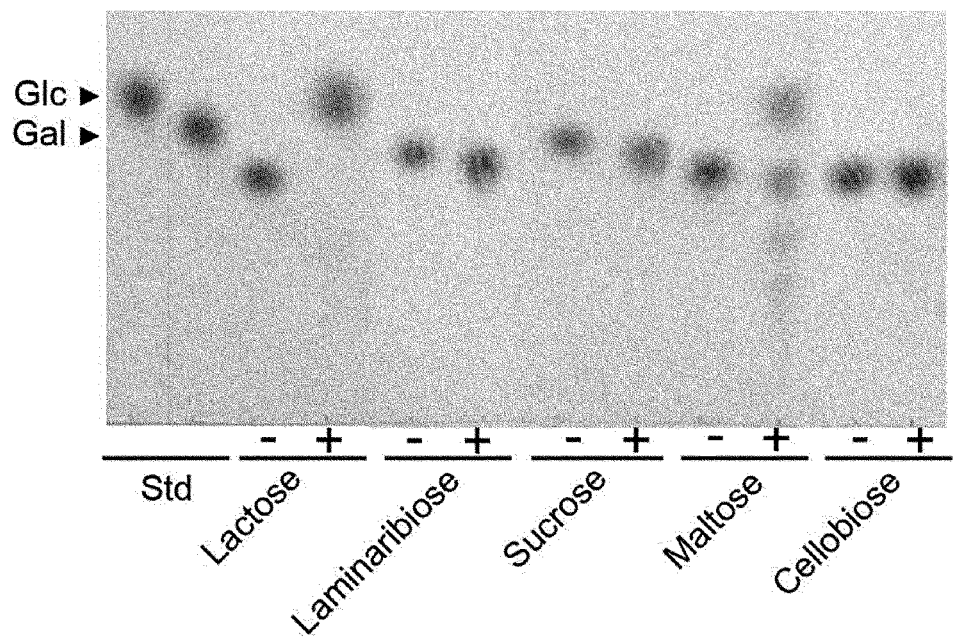
FIG. 3 illustrates the substrate specificity of VeFUC shown as a TLC analysis result of reaction products obtained by incubating VeFUC with biomass-derived substrates including lactose, laminaribiose, sucrose, maltose and cellobiose at 303 K for 30 minutes. Glucose (Glc) and Galactose (Gal) were used as markers for reaction products (Std, Standard material; −, Substrate only; +, reaction results of VeFUC with substrates).

In order to measure kinetic parameters of VeFUC for pNP-α-L-Fuc, the enzymatic reaction was performed at 313 K in 10 mM sodium acetate buffer solution (pH 6.0) by varying the substrate concentration. The kinetic parameters of VeFUC were measured using the Lineweaver-Burk plot. The $V_{max}$, $K_m$, and $k_{cat}$ values of VeFUC for pNP-α-L-Fuc were 24.8±0.9 U mg$^{-1}$ protein, 6.34±0.48 mM and 4.81±1.8 s$^{-1}$, respectively. The catalytic constants for VeFUC were within a normal range of other characterized bacterial fucosidase (Table 1).

hydrolyzed by VeFUC (FIG. 3). However, VeFUC did not hydrolyze sucrose formed by D-glucose and D-fructose units having α-1,2 glycosidic bonds, laminaribiose having β-1,3-glycosidic bonds and cellobiose with β-1,4-glycosidic bonds. These results suggest that VeFUC has α-fucosidase, α-1,4-glucosidase and β-1,4-galactosidase activities, but does not have α-galactosidase and β-glucosidase activities.

<Experimental Example 2> Characterization of VeFUC

In order to test the effect of pH and temperature on the enzyme activity of VeFUC, 10 mM pNP-α-L-Fuc, 10 mM lactose and 10 mM maltose were incubated with 4 nmol VeFUC at various pHs (pH 4.0 to 10.0) and temperatures (293 to 343 K).

Figure 4A:
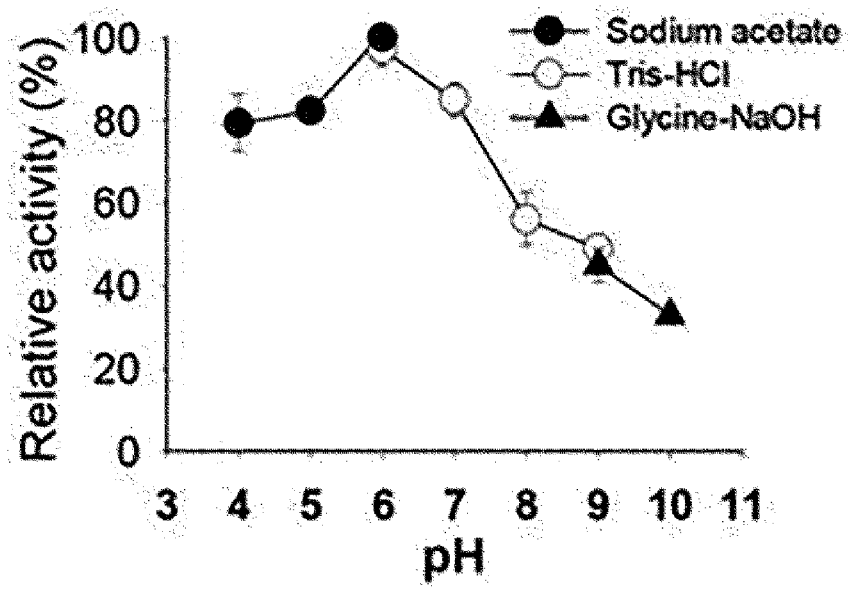
FIGS. 4A-4I illustrate the effects of pH and temperature on enzymatic reactions.
Figure 4B:
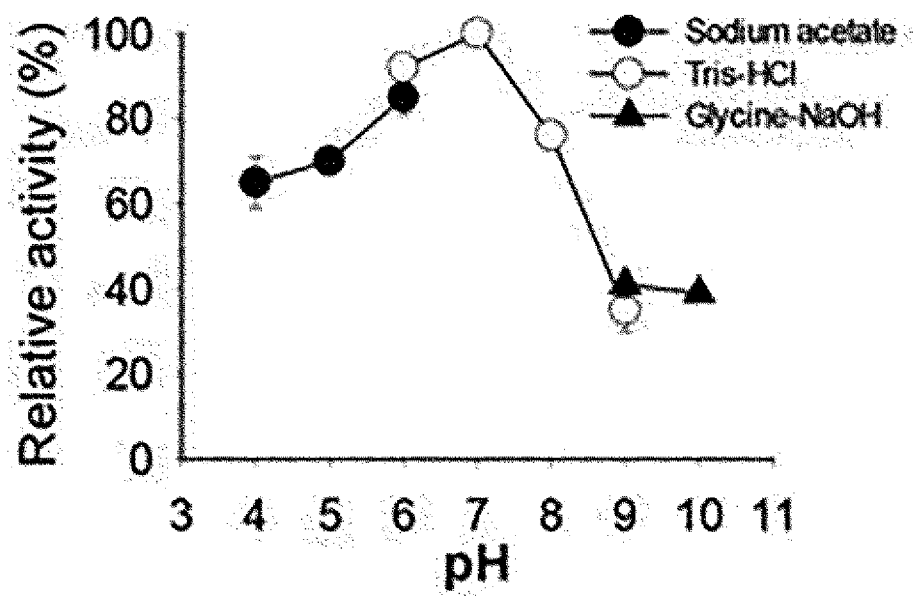
Figure 4C:
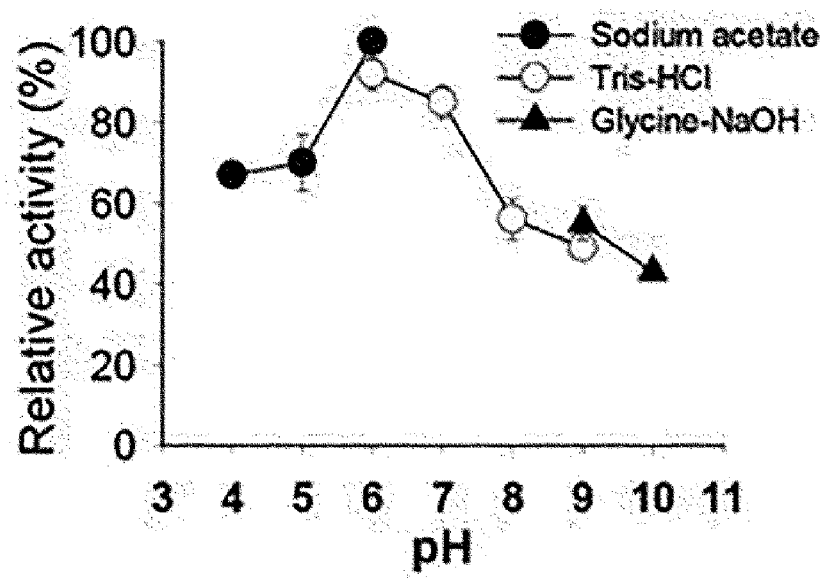
Figure 4D:
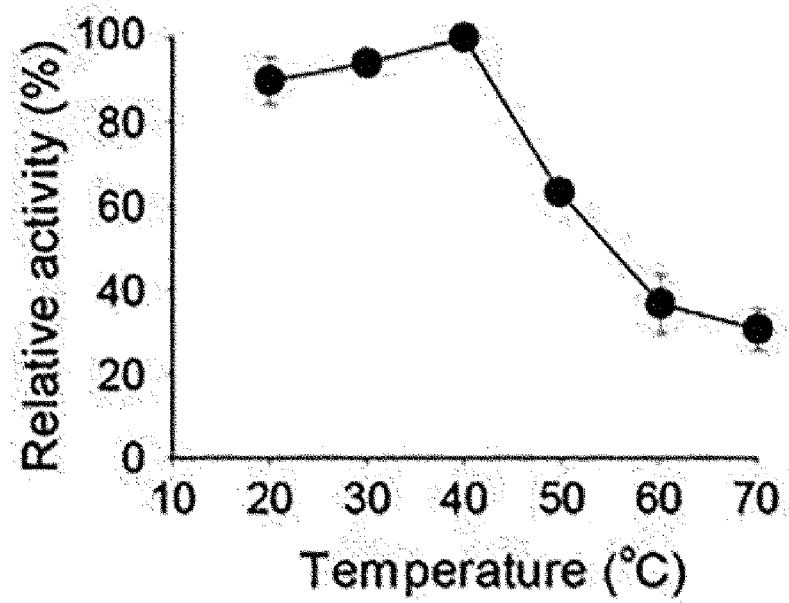
Figure 4E:
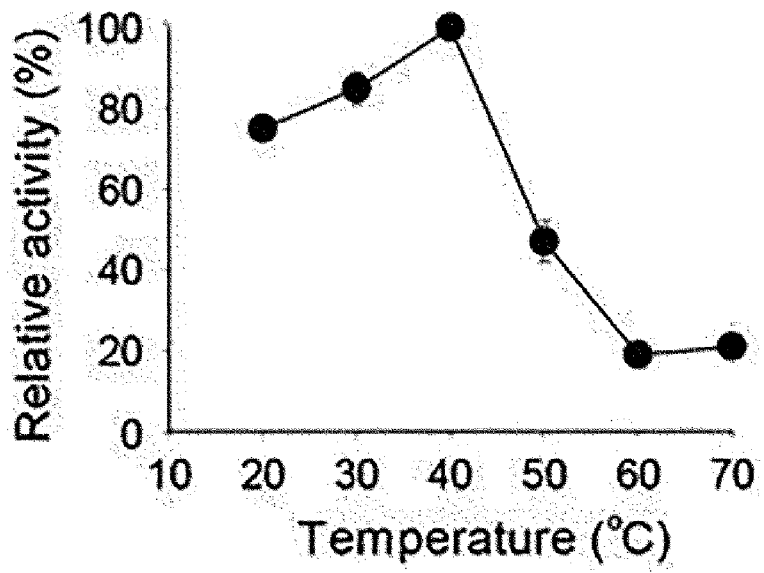
Figure 4F:
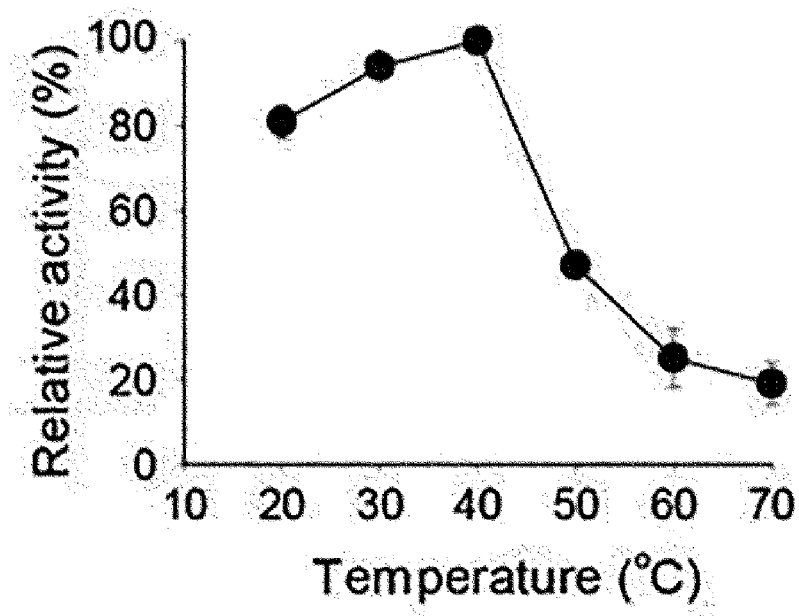

The highest activity of VeFUC for pNP-α-L-Fuc, maltose and lactose was obtained at pH 6.0 in 10 mM sodium acetate buffer solution, pH 7.0 in 10 mM Tris-HCl buffer solution, and pH 6.0 in 10 mM sodium acetate buffer solution, respectively (FIGS. 4A to 4C). The optimum temperature for VeFUC enzyme activity was measured to be approximately 313 K for all the substrates (FIGS. 4D to 4F). According to

TABLE 1

Kinetic parameters of representative bacterial fucosidase

| Protein | Species name | Substrate | Vmax | Km | Kcat | Remarks |
| --- | --- | --- | --- | --- | --- | --- |
| VeFUC | V. EJY3 | pNP-α-L-Fuc | 24.8 ± 0.9 | 6.34 ± 0.48 | 4.81 ± 1.8 | Present invention |
| BT_2970 | B. subtilis thetaiotaomicron | pNP-α-L-Fuc | — | 1.5 | 1.3 | Sakurama, H. et al. Biosci. Biotechnol. Biochem. 2012, 76, 1022-1024. |
| AlfA | Lactobacillus casei | pNP-α-L-Fuc | 1.14 | 0.27 | — | Rodriguez-Diaz, J. et al. Appl. Environ. Microbiol. 2011, 77, 703-705 |
| AlfB | L. casei | pNP-α-L-Fuc | 6 | 2.9 | — | Rodriguez-Diaz, J. et al. Appl. Environ. Microbiol. 2011, 77, 703-705 |
| AlfC | L. casei | pNP-α-L-Fuc | 22.2 | 5.3 | — | Rodriguez-Diaz, J. et al. Appl. Environ. Microbiol. 2011, 77, 703-705 |
| aLfuk1 | P. aeruginosa thiaminolyticus | pNP-α-L-Fuc | — | 0.44 ± 0.02 | — | Benesova, E. et al. Glycobiology. 2013, 23, 1052-1065 |
| TM0306 | T. maritima | pNP-α-L-Fuc | — | 0.034 ± 0.002 | 5.4 ± 0.2 | Sulzenbacher, G. et al. J. Biol. Chem, 2004, 279, 13119-13128 |
| TfFuc1 | Tannerella forsythia | pNP-α-L-Fuc | 20.4 ± 0.8 | 0.67 ± 0.2 | — | Megson, Z. A. baumannii et al. Virulence, 2015, 6, 282-292 |
| XCC2888 | Xanthomonas campestris | pNP-α-L-Fuc | — | 0.7 ± 0.1 | 6.1 ± 2.0 | Dupoiron, S. et al. J. Biol. Chem, 2015, 290, 6022-6036 |
| Alf1_Wf | Wenyingzhuangia fucanilytica | pNP-α-L-Fuc | 4.75 ± 0.38 | 3.30 ± 0.42 | 5.44 | Dong, S. et al. Protein Expr. Purif., 2017, 129, 9-17. |

Figure 4G:
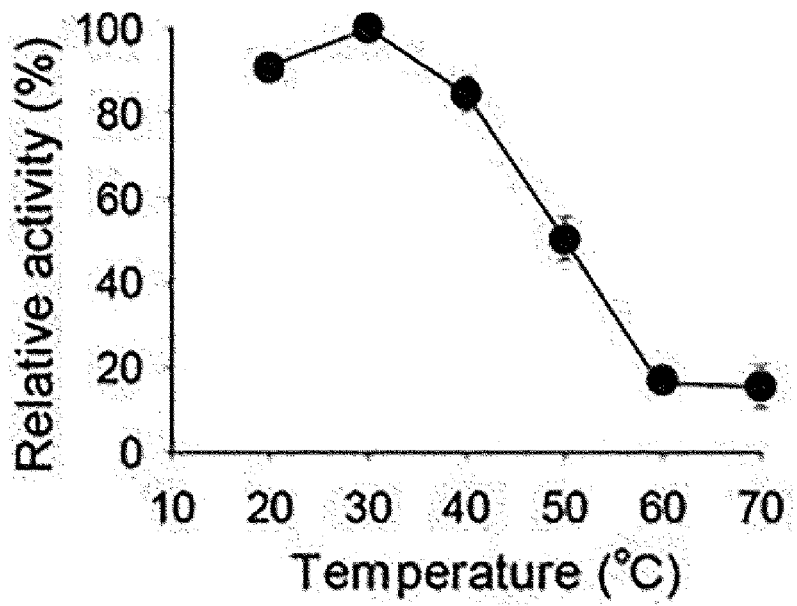
Figure 4H:
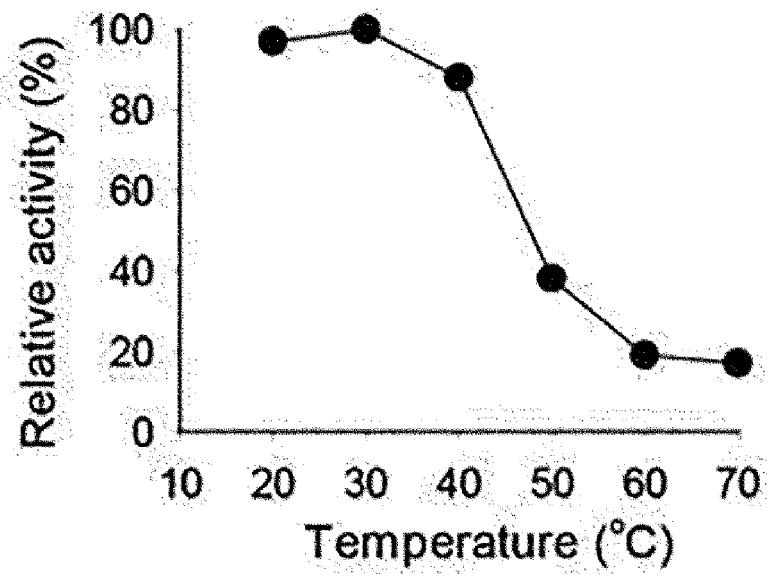
Figure 4I:
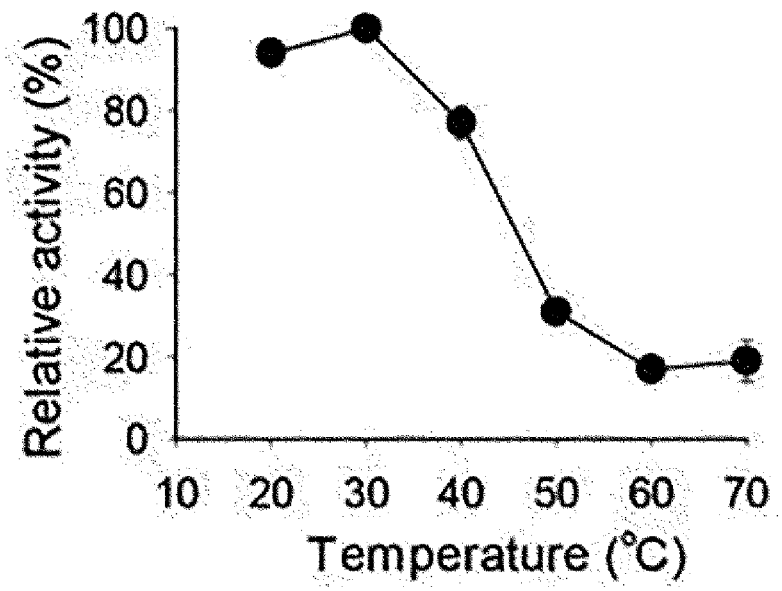

Further, enzymatic reactions were performed with several 10 mM disaccharides having various types of glycosidic bonds. Among the disaccharide groups, lactose (β-1,4-glycosidic bond) and maltose (α-1,4-glycosidic bond) were the results in the thermal stability test, VeFUC was stable at a temperature of 303 K or less after the pre-incubation for 60 minutes, but relative activity decreased after the pre-incubation at a temperature higher than 303 K (FIGS. 4G to 4I).

<Experimental Example 3> Action Mode of VeFUC

Figure 5:
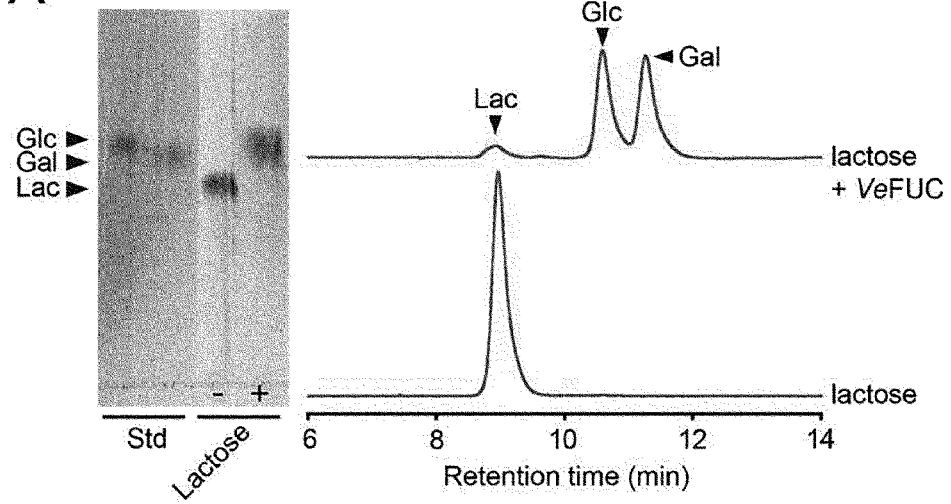
FIG. 5 illustrates the TLC (left) and HPLC (right) analysis results of VeFUC enzymatic reaction substrates using lactose (A) and maltose (B) as substrates. Reactions were performed in 20 mM Tris-HCl (pH 7.0) at 313 K for 120 minutes. Glucose (Glc) and Galactose (Gal) were used as markers for reaction products (Std, Standard material; -, Substrate only; +, reaction results of VeFUC with substrates).
Figure 5:
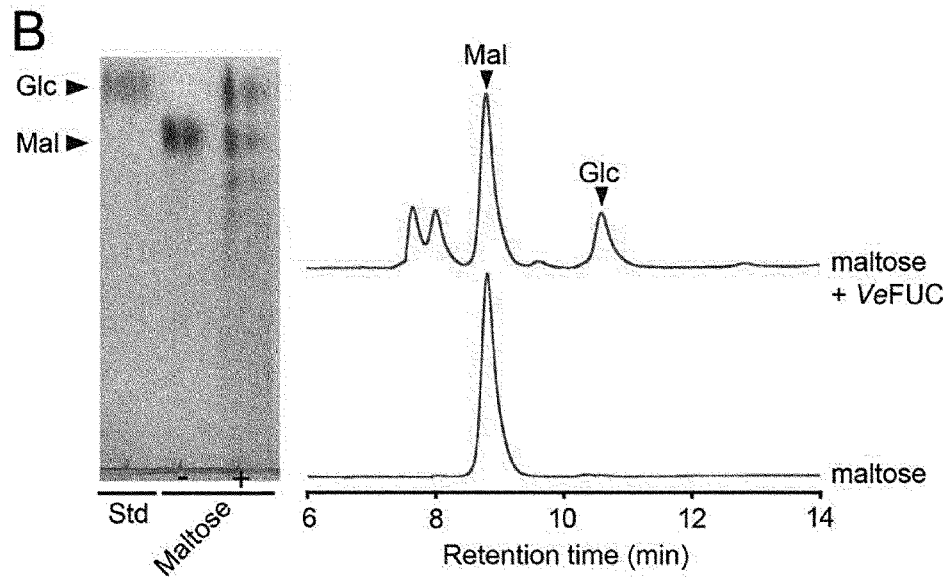

Under optimized reaction conditions, VeFUC reaction products incubated with lactose and maltose were analyzed by TLC and HPLC. When lactose was used as a substrate, glucose and galactose were produced (A of FIG. 5). These results suggest that VeFUC hydrolyzes the β-1,4-glycosidic bonds of lactose by B-galactosidase activity. When maltose was used as a substrate, a higher degree of polymerization than each of glucose and the substrate was formed due to a-glucosidase and transglycosylation activity (B of FIG. 5). To date, VeFUC is the first enzyme which exhibits dual catalytic activity capable of hydrolyzing α- and β-glycosidic bonds, which are not fucosylated, by α-1,4 glucosidase and β-1,4 galactosidase activities.

Figure 6:
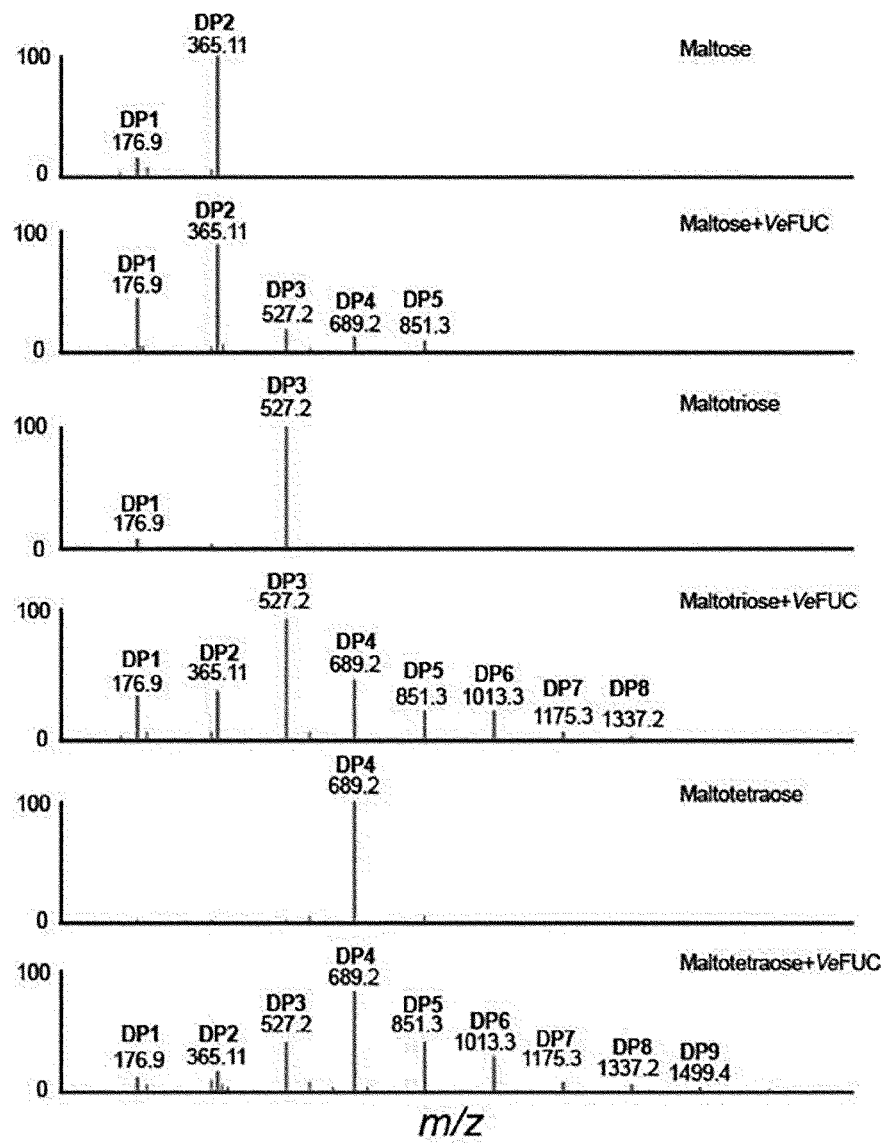
FIG. 6 illustrates the transglycosylation activity of VeFUC. The enzymatic reaction products of VeFUC with maltose (DP2), maltotriose (DP3) and maltotetraose (DP4) were analyzed by MALDI-TOF/MS. Reactions were performed in 10 mM Tris-HCl (pH 7.0) at 313 K for 60 minutes.

In order to investigate the transglycosylation activity of VeFUC, a reaction mixture of VeFUC incubated with maltose (DP2), maltotriose (DP3) or maltotetraose (DP4) was analyzed by MALDI-TOF/TOF MS. Oligosaccharides having a higher degree of polymerization than the substrate were detected in all reaction mixtures using DP2, DP3 and DP4 as substrates (FIG. 6). The reaction products obtained using maltose as a substrate showed that VeFUC primarily hydrolyzed maltose to glucose (DP1, 176.9 m/z) and formed oligosaccharides ranging up to DP5 (DP3, 527.1 m/z; DP4, 689.2 m/z; DP5, 851.3 m/z). When maltotriose and maltotetraose were used as substrates, VeFUC formed oligosaccharides of DP8 and DP9, respectively (FIG. 6).

Many representative GH29α-L-fucosidases found in bacteria and eukaryotes have shown their ability to catalyze transfucosylation reactions with different efficiencies. To date, pNP-α-L-Fuc has been used as a fucosyl donor for most transfucosylation reactions. Interestingly, VeFUC showed high transglycosylation activity for α-1,4-oligosaccharides (FIG. 6). According to this result, glucose released from the non-reducing end of a substrate is delivered to a substrate having α-1,4 regioselectivity. Therefore, the substrate maltose can be provided as both a donor and an acceptor (self-condensation) and thus can form oligosaccharides having a higher degree of polymerization than the substrate. Maltooligosaccharides produced from the transglycosylation activity of VeFUC are high-value-added functional oligosaccharides which are potentially applicable in the food industry due to their mild sweetness, relatively low osmotic pressure, high moisture-retention ability and appropriate viscosity, and their ability to suppress crystallization and delay staling of bread.

The present invention efficiently produces maltooligosaccharides having a high degree of polymerization, and thus can be applied to the development of high value-added new materials in the food industry.

What is claimed is:

1. A composition for producing monosaccharides or maltooligosaccharides, comprising:
   α-L-fucosidase comprising an amino acid sequence of SEQ ID NO: 1; and
   one or more substrates selected from the group consisting of lactose and maltooligosaccharides having a degree of polymerization of 2 or higher,
   wherein the α-L-fucosidase is obtained from a host cell transformed with a recombinant vector comprising a gene encoding the α-L-fucosidase.

2. The composition of claim 1, wherein the α-L-fucosidase has α-1,4 glucosidase and β-1,4 galactosidase activities and transglycosylation activity.

3. The composition of claim 1, wherein the gene encoding the α-L-fucosidase is derived from *Vibrio* sp. strain EJY3 having accession number KCTC11976BP.

4. The composition of claim 1, wherein the gene comprises a base sequence of SEQ ID NO: 2.

5. The composition of claim 1, wherein the monosaccharides comprise glucose or galactose.

6. The composition of claim 1, wherein maltooligosaccharides having a degree of polymerization of 2 to 4 are used as the substrate.

7. A method for producing monosaccharides or maltooligosaccharides, comprising:
   reacting one or more substrates selected from the group consisting of lactose and maltooligosaccharides having a degree of polymerization of 2 or higher with α-L-fucosidase comprising an amino acid sequence of SEQ ID NO: 1; and
   collecting monosaccharides and maltooligosaccharides from a reaction product, wherein the maltooligosaccharides have a higher degree of polymerization than that of maltooligosaccharides used as the substrate.

8. The method of claim 7, wherein the reaction is performed under conditions of 30 to 40° C. and a pH of 6 to 8 for 30 minutes to 48 hours.

9. The method of claim 7, wherein maltooligosaccharides having a degree of polymerization of 2 to 4 are used as the substrate.

10. The method of claim 7, wherein the monosaccharides comprise glucose or galactose.

* * * * *

```
                        SEQUENCE LISTING

<160> NUMBER OF SEQ ID NOS: 4

<210> SEQ ID NO 1
<211> LENGTH: 607
<212> TYPE: PRT
<213> ORGANISM: Vibrio sp.

<400> SEQUENCE: 1

Met Thr Lys Pro Thr Ala Gly Glu Leu Thr Gly Thr Ser Ser Gln Ala
1               5                   10                  15

Thr Ser Gln Leu Asp Asn Arg Asn Ala Phe Thr Gly Val Ser Lys Gln
            20                  25                  30

Gly Leu Asn Arg Trp Lys Lys Asn Thr Phe Gly Met Phe Ile His Trp
        35                  40                  45

Gly Leu Tyr Cys His Arg Asp Leu Ala Gly Tyr Tyr Gln Gly Gln Tyr
    50                  55                  60

Tyr Asp Ile Ile Ser Glu Trp Leu Pro His Phe Ala Arg Ile Pro Met
65                  70                  75                  80

Arg Asp Tyr Lys Glu Tyr Ala Ser Asp Phe Asn Pro Ser Glu Phe Asp
                85                  90                  95

Ala Asp Gln Val Thr Ala Leu Ala Lys Thr Ala Gly Met Asn Tyr Met
            100                 105                 110

Val Val Thr Ala Lys His His Asp Gly Phe Ala Met Tyr His Ser Pro
        115                 120                 125

Ser His Pro Phe Asn Ile Thr Asp Ala Thr Pro Phe Lys Arg Asp Pro
    130                 135                 140

Val Ala Glu Leu Ser Gln Ser Cys Arg His Lys Asp Leu Asp Phe Gly
145                 150                 155                 160

Leu Tyr Tyr Ser His Val Ile Asp Trp Glu Asn Glu Asn Ala Val Ser
                165                 170                 175

Lys Ala Pro Asn Asp Trp Asp Phe Asn Pro Asp Gln Ala Asn Tyr Gln
            180                 185                 190
```

-continued

Glu Tyr Trp Asn Asn Lys Cys Leu Pro Gln Val Asn Glu Leu Leu Glu
            195                 200                 205

Gln Tyr Gly Asp Leu Cys Ser Leu Trp Phe Asp Met Gly Gly Phe Asp
    210                 215                 220

Val Gln Glu Glu Ala Asp His Val Arg Arg Ile Gly Glu Leu Met Ala
225                 230                 235                 240

Leu Ile Arg Lys Lys Gln Pro Asp Ala Val Asn Ser Arg Val Thr
                245                 250                 255

Ala Pro Glu Cys Glu Tyr Gln Leu Asp Trp Asp Ile Lys Thr Gly His
            260                 265                 270

Asp Asn Tyr Met Glu Pro Leu Tyr Ile Lys Pro Tyr Tyr Trp Glu Gly
        275                 280                 285

Ile Ala Thr Ser Asn Asp Asn Trp Gly Tyr Ser Arg Asn Asp Asn Asn
    290                 295                 300

Thr Lys Ser Ser Lys Asp Leu Ile Asn Gln Leu Cys Ser Val Val Ser
305                 310                 315                 320

Arg Gly Gly Asn Phe Leu Leu Asn Ile Thr Leu Asp His Asn Gly Arg
                325                 330                 335

Ile Pro Gln Ser Leu Val Arg Leu Leu Ser Glu Ile Gly Gln Trp Met
            340                 345                 350

Gln Val Asn Gln Glu Ala Val Ile Asp Thr Glu Ala Thr Pro Leu Gln
        355                 360                 365

Thr Gly Phe Asn Trp Gly Val Val Thr His Arg Pro Ala Thr Asn Lys
    370                 375                 380

Leu Tyr Leu His Val Gln Arg Gln Pro Glu Gln Asn Val Ile Cys Leu
385                 390                 395                 400

His Ser Leu Asn Asn Arg Ile Lys Gln Val Arg Leu Leu Asp Asn Gln
                405                 410                 415

Ile Lys Gly His Val Ser Tyr Leu Gln Lys Thr His Thr Asp Thr Gly
            420                 425                 430

Ile Thr Ala Ser Thr Leu Asn Leu Gln Leu Gly His Asn Tyr Asp Arg
        435                 440                 445

Met Pro Leu Val Ile Glu Leu Glu Tyr Asp Gly Glu Leu Asp Ile Asn
    450                 455                 460

Pro Ile Val His Gln Asp Arg Leu Ala Lys Val Arg Leu Asp Thr Leu
465                 470                 475                 480

Asn Ile Ala His Phe Asp Pro Glu Lys Leu Thr Tyr Arg Trp Thr Phe
                485                 490                 495

Gln Ile Gln Ser Pro Gly Arg Phe Ala Leu Asp Leu Val Ser Leu Glu
            500                 505                 510

Thr Met His His Lys Asp Pro Gln Trp Val His Asn Gly Lys Thr Gly
        515                 520                 525

Arg Ile Ser Cys Gly Gly Gln Ser Trp Glu Phe Glu Leu Asn Leu Asp
    530                 535                 540

Lys Thr Asp Thr Asn Asp Ala Gln Val Pro Trp Lys Asn Ile His Ser
545                 550                 555                 560

Arg Leu Gly Glu Leu His Phe Pro Gln Ala Gly Glu Tyr Thr Leu Glu
                565                 570                 575

Phe Ser Glu Leu Pro Leu Ala Ile Asp Gln Ser Glu Lys Tyr Gly Gln
            580                 585                 590

Asp Tyr Ile Asn Leu Glu Tyr Leu Gln Leu Gly Pro Arg Leu Ala
        595                 600                 605

<210> SEQ ID NO 2
<211> LENGTH: 1824
<212> TYPE: DNA
<213> ORGANISM: Vibrio sp.

<400> SEQUENCE: 2

```
atgaccaagc ccacagcagg tgagctgaca ggaacaagca gccaggctac aagccagttg      60
gacaatcgca atgcctttac tggcgtcagt aagcaagggc tgaaccgctg gaaaaaaaat     120
acctttggca tgtttatcca ctgggggctt tattgccacc gggatctggc cgggtattat     180
cagggacaat actacgacat cattagcgaa tggctgcccc actttgcccg tattcctatg     240
cgggactaca agaatacgc ttctgacttt aaccctagcg aatttgatgc cgaccaggta     300
acggcgttgg ccaaaacagc cgggatgaat tacatggtgg tcacagctaa gcatcacgac     360
gggtttgcca tgtatcacag cccatcacat cctttcaaca tcacagacgc cacaccgttt     420
aaacgcgatc cagtcgcaga actcagtcaa agctgtcgtc ataaggactt ggattttggc     480
ctgtattatt cgcatgtgat cgactgggag aacgaaaacg cagtgtcaaa agcccccaat     540
gattgggact caacccaga ccaagccaat tatcaggaat actggaataa caagtgctta     600
cctcaggtta atgaattgct tgagcagtac ggagatctat gttcgctgtg gtttgatatg     660
ggaggctttg atgtacaaga agaagctgac cacgtacgtc ggatcggcga actgatggca     720
ttaatccgga aaaacagcc tgatgcgtg gttaatagcc gagttacggc accggaatgt     780
gagtaccagt tggattggga tattaaaacc ggccatgata actacatgga ccactttat     840 atcaagccat attactggga aggcattgct ccagtaatg acaactgggg ttatagccgc     900
aacgacaaca ataccaaatc cagtaaggat ctgataaacc agctgtgttc tgtagtcagc     960
cggggcggaa actttctgct caatataact ctggatcata cgggcgtat tcccccagtcc    1020 cttgtcgcat tacttagcga gataggccaa tggatgcagg tgaatcagga agcggtgatc    1080
gatacagaag ctaccccgct gcagaccggc ttcaattggg gcgtggtaac acatagacca    1140
gccaccaata agctgtatct gcatgtgcag cgtcagccag agcaaaacgt tatctgctta    1200
catagtctca ataatcgaat caaacaggtg cgattgcttg ataatcaaat caaaggccat    1260
gtttcctatt tgcagaaaac acatacggat acgggcatca cggccagcac cctcaacctg    1320
caactcgggc acaattatga tcggatgcct ctggtgatcg agctggagta tgacggtgag    1380
ctggacatca atcctatcgt ccatcaggac cgactggcca aagtgcgcct ggacacgctc    1440
aatatcgctc actttgatcc tgaaaaactc acttaccgct ggaccttcca aattcagagc    1500
ccgggccggt tcgccttaga tctggttcct ttggaaacca tgcatcataa agaccctcaa    1560
tgggtacaca acggtaaaac cggtcgcata agttgtggag gtcagtcttg ggagtttgag    1620
ctaaacctcg acaaaacaga caccaacgat gcccaggtac cgtggaaaaa cattcacagt    1680
cgcttgggcg agctgcattt tccccaagcc ggtgaatata cactggagtt cagcgagttg    1740
ccgctggcta tcgatcagtc tgagaaatat ggtcaggatt acattaatct tgaatatctg    1800
cagttgggcc ccgcttggc gtga                                            1824
```

<210> SEQ ID NO 3
<211> LENGTH: 31
<212> TYPE: DNA
<213> ORGANISM: Artificial Sequence
<220> FEATURE:
<223> OTHER INFORMATION: Forward primer for amplification of VEJY3_11310

```
<400> SEQUENCE: 3
gcgggatcca tgaccaagcc cacagcaggt g                                 31

<210> SEQ ID NO 4
<211> LENGTH: 48
<212> TYPE: DNA
<213> ORGANISM: Artificial Sequence
<220> FEATURE:
<223> OTHER INFORMATION: Reverse primer for amplification of VEJY3_11310

<400> SEQUENCE: 4
gcgctcgagg tggtggtggt ggtggtgcgc caagcggggg cccaactg               48
```